United States Patent [19]

van de Werken

[11] Patent Number: Plant 7,533

[45] Date of Patent: May 28, 1991

[54] FORSYTHIA PLANT NAMED 'FAIRY-LAND'

[75] Inventor: Hendrik van de Werken, Knoxville, Tenn.

[73] Assignee: The University of Tennessee Research Corporation, Knoxville, Tenn.

[21] Appl. No.: 271,665

[22] Filed: Nov. 16, 1988

[51] Int. Cl.[5] ..... A01H 5/00

[52] U.S. Cl. ..... Plt./54

[58] Field of Search ..... Plt./54

[56] References Cited

PUBLICATIONS van de Werken (1988) "Mutant Offspring", *American Nurseryman*, vol. 167, No. 1 (Jan. 1, 1988) pp. 127-132.

Fincham, J. R. S., "Ionizing Radiation", *Genetics*, Jones and Bartlett Publishers, Inc., Boston, 1983, pp. 326-333.

Decourtye, L. (1978) "Utilisation de la mutagenese pour l'obtention de nouvelles varietes d'arbustes ornementaux", Comptes Rendus des Seances de l'Academie d'Agriculture de France, vol. 64 (8), pp. 664-669.

"Arnoldia," vol. 31, No. 2, The Arnold Arboretum, Mar. 1971, pp. 41-63.

"Flowering Shrubs," Zucker, Isabel, 1966, D. Van Nostrand Co., Inc., New York, N.Y., p. 380.

"Hilliers Manual of Trees & Shrubs," 2nd American Edition, Hilliers & Sons Ltd., 1979, A. S. Barnes & Co., Cranbury, N.J., p. 575.

"Hortus Third, A Concise Dictionary of Plants Cultivated in the United States and Canada," Staff of L. H. Bailey Hortorium, Cornell University, 1976, MacMillan Publishing Co., New York, N.Y., p. 1290.

"Manual of Woody Landscape Plants—Their Identification, Ornamental Characteristics, Propagation and Uses," Dirr, Michael A., 1983, Stipes Publishing Co., Champaign, Ill., p. 826.

*Primary Examiner*—James R. Feyrer

*Attorney, Agent, or Firm*—William H. Elliott, Jr.

[57] ABSTRACT

A new cultivar of Forsythia named 'Fairy-Land' characterized by its relatively small shrub size, its small lanceolate foliage, and the varying number, between four and eight, of petals on its flowers.

3 Drawing Sheets

This invention relates to a new cultivar of Forsythia named "Fairy-Land", which is characterized especially by its small overall size, its simple, minimally serrate, lanceolate foliage, and the varying number of flower petals, from four to eight, on a single corolla.

The new variety was derived as a seedling from a vegetative line of mutants, which had been produced in turn by subjecting rooted cuttings of the parent *Forsythia intermedia* 'Lynwood Gold' (a sport of *F. intermedia* "Spectabilis") to irradiation with 1,200 rad fast neutrons.

In 1968, three hundred cuttings of "Lynwood Gold" that had been potted and held in cold storage (38° F.) for six weeks and then returned to the greenhouse for two days were irradiated with 1200 rad fast neutrons. One of the plants of this group that broke dormancy formed a shoot with variegated foliage. This plant was cut back repeatedly to induce branching and eventually formed shoots that exhibited different characteristics. Each shoot was propagated by stem cuttings over 10 vegetative generations of selection and propagation. From this plant population two vegetatively selected types and three seedlings were selected. Further propagation and testing of these selections over several more years were shown to be the stable and new forsythia varieties that are the subject of this and four other copending plant patent applications; viz:

| Ser. No. | Name | Type |
|---|---|---|
| 272,063 | "Lemon-Screen" | vegetative selection |
| 273,489 | "Tinkle Bells" | vegetative selection |
| 271,919 | "Minikin" | seedling |
| 271,665 | "Fairy Land" | seedling |
| 271,666 | "Pygmy-Red" | seedling |

Each differs greatly from the parent "Lynwood Gold" and also from one another.

"Fairy-Land" was selected at the seedling stage because of its bright green color, small linear foliage, and short internodes. Cuttings from this plant have been rooted in soil and asexually propagated, and its progeny have displayed homogeneous and stable characteristics.

Throughout this specification, color names beginning with a small letter signify that the name of the color as used in common speech are aptly descriptive. Color names beginning with a capital letter designate values based on the R.H.S. Colour Chart, published by The Royal Horticultural Society of London, England.

The accompanying drawings illustrate the new variety in color as grown in Knox County within the State of Tennessee.

Figure 1:
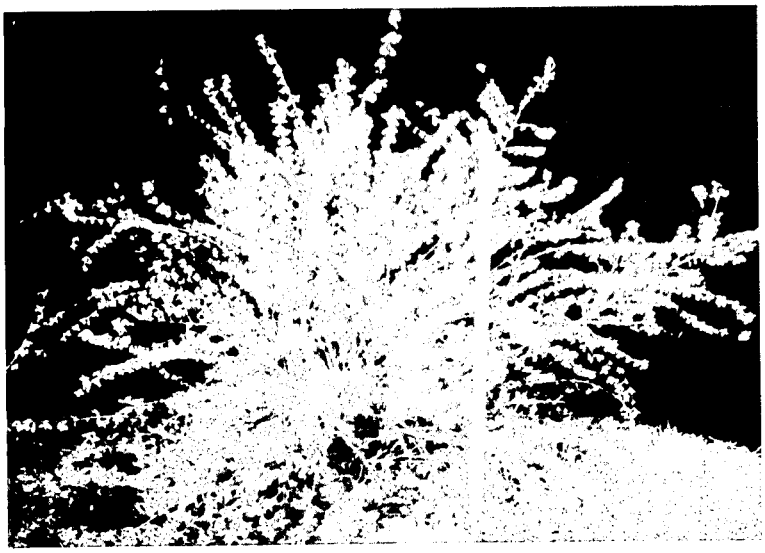
FIG. 1 illustrates "Fairy-Land" as a 5½ old plant in bloom in the spring.
Figure 2:
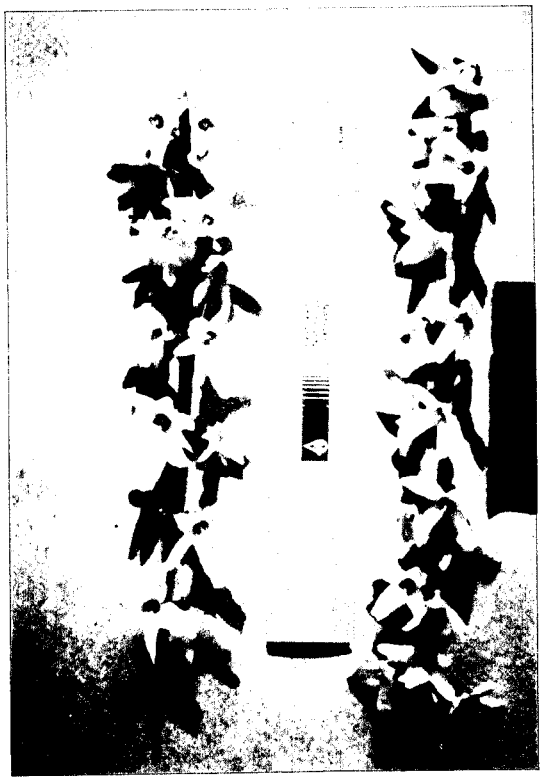
FIG. 2 shows flowered cut stems of "Fairy-Land".
Figure 3:
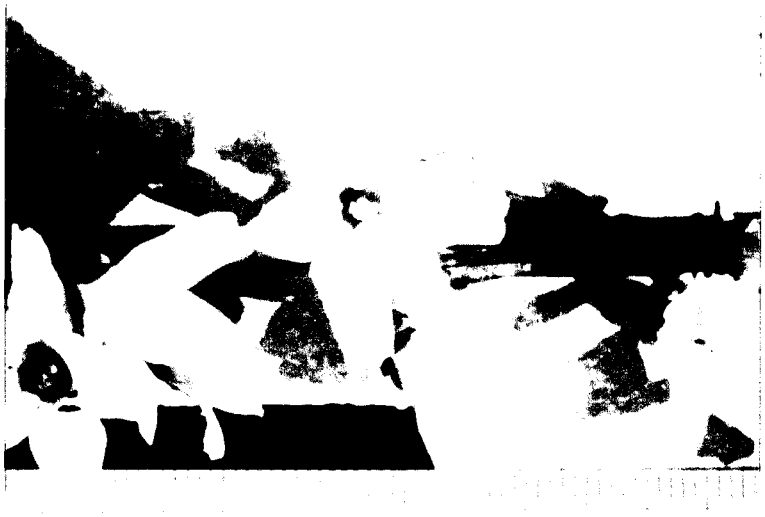
FIG. 3 is a close-up view of the flowers of FIG. 2.
Figure 4:
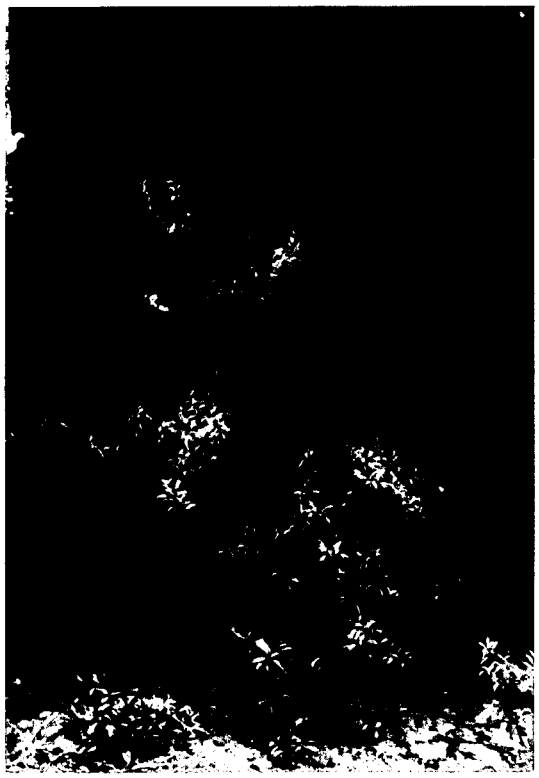
FIG. 4 illustrates the "Fairy-Land" plant in summer foliage.
Figure 5:
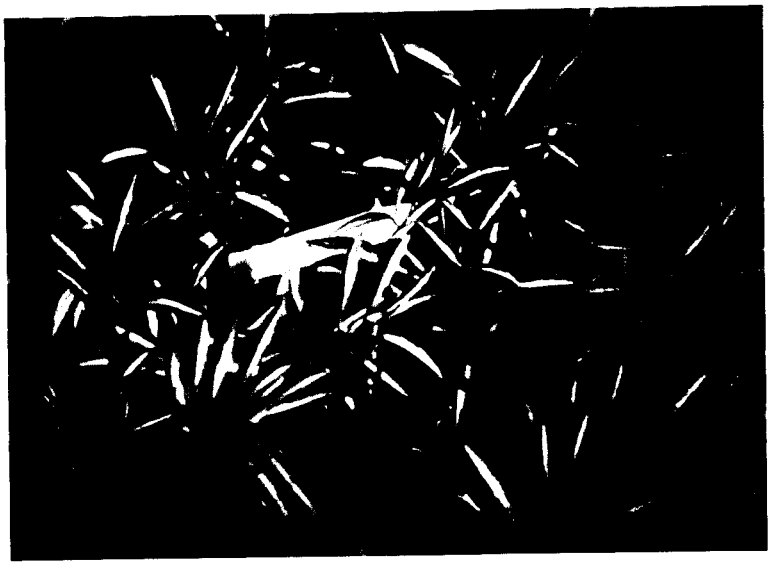
FIG. 5 is a closer view of the foliage shown in FIG. 4. The white label is 0.6 in. wide and 5 inches long.

The following characteristics distinguish "Fairy-Land" from its parent and other Forsythia cultivars:

THE PLANT

"Fairy-Land", because of its small overall stature (3' to 4' in height and 5' to 6' in width at maturity) and dense foliage as a young plant, is very well suited for culture in nursery plant containers. The plant exhibits good vigor for its size, is hardy to Zone 6b (or lower) and develops few seed pods. The low, broad, attractively dense and fine textured "Fairy-Land" plant form, both in bloom and when in leaf, make this cultivar suitable for a wide range of landscape applications.

Its parent, "Lynwood Gold", by contrast is tall and slender—a straight upright variety with erect stems and which attains a height of 6 ft. to 7½ ft. at maturity.

"Fairy-Land" is suited for applications ranging from mass planting and area delineation to use as a container plant on patios and plazas. Whereas, "Fairy-Land" shares several characteristics with the related Minikin cultivar, "Fairy-Land" is distinguished from Minikin in its somewhat larger shrub size, larger foliage, larger flowers, and in the larger average number of petals per flower.

FLOWER

"Fairy-Land" flowers at an intermediate date with deep yellow flowers (Yellow 6A) about ¾" to 1¼" in width and appear two to four per node, the internodes being ½ in. to 1 in. long. Although the flower petals generally number four, many of the blooms have five, six, seven, or eight petals on a single corolla. The corolla lobes are small and reflexed. The pistils extend 3/25 in. to 4/25 in. above the pollen sacs of the stamen.

The "Lynwood Gold" parent is fertile and has pistils that extend well above its pollen sacs, is late flowering and its medium sized flowers (about 1" to 1½" in diameter) are almost evenly spaced on the stem. The flowers of "Lynwood Gold" are brilliant yellow (lighter than its parent, F. Spectabilis). The corolla lobes of "Lynwood Gold" are reflexed and its petals are large, broad open and elliptic.

SHOOTS

The shoots of "Fairy-Land" are light green when young and brownish green when mature. Its pith is slightly lamellate between nodes.

The stems of the "Lynwood Gold" parent are green when young and brown when mature; they are a bit stiff; the pith at the nodes is lamellate, and on one year shoots, the stems between nodes are hollow.

FOLIAGE

The leaves of "Fairy-Land" are a rather light medium green on both young and mature plants. In the fall they are mostly faded yellow. The leaves are simple, lanceolate, acuminate at the tip and attenuate at the base. The leaves on flowering wood are 0.2 to 0.4 in. wide and 1½ to 2½ in. long and not serrate. On vegetative shoots the leaves are 0.5 in. to 0.6 in. wide and about 3 in. long and serrate on the top ⅓. Leaf venation is pinnate. A fine textured appearance results from closely spaced foliage, particularly on the flowering wood, where the internodes are generally ¼ in. to less than 1 in.

The leaves of the "Lynwood Gold" parent, on the other hand, are ovate lanceolate in shape and about 3" to 4½" long and about 1" to 1½" wide. Both young and old leaves are deep green in color.

To facilitate the comparison of the characteristics and features of "Fairy-Land", the subject of this application, and its parent, "Lynwood Gold" and also with the four other new mutant offspring varieties of "Lynwood Gold" referred to above, there are attached hereto as Tables 1-5 comparative tabulations of the characteristics and properties of parent and its five offspring mutants that were developed from a single irradiated plant of "Lynwood Gold." Table 1 compares "Fairy-Land" and its parent "Lynwood Gold". Table 2 compares "Fairy-Land" and "Pygmy-Red". Table 3 compares "Fairy Land" and "Tinkle Bells". Table 4 compares "Fairy-Land" and "Minikin". Table 5 compares "Fairy-Land" and "Lemon Screen".

TABLE 1

| Ser. No. 271,665 | |
|---|---|
| **FAIRY LAND** | |
| Plant | |
| Habit | Small overall & fine textured: Closely spaced flowers & leaves Dense (young) foilage |
| Size, height | 3'-4' |
| Size, width | 5'-6' |
| Vigor | Good vigor for size |
| Hardiness | Zone 6b (or lower) |
| Productivity | Few seed pods |
| Stems | |
| Color (young) | Light green |
| Color (mature) | Brownish green |
| Rigidity | Very flexible lamellate between nodes |
| Leaves | |
| Type | Simple |
| Color | |
| (young) | Medium green (fairly light) |
| (mature) | Medium green (fairly light) |
| (fall) | Mostly faded yellow |
| Shape | Lanceolate |
| tip | Accuminate |
| base | Attenuate |
| margins | On flowering wood: entire On vegetative wood: serrate top ⅓ |
| Size | |
| length | On flowering wood: 1½"-2½" On vegatative shoots: about 3" |
| width | On flowering wood: 0.2"-0.4" On vegetative shoots 0.5-0.6" |
| Venation | Pinnate |
| Flower | |
| Date of Flowering | Intermediate |
| Size: width | ¾"-1¼" |
| Color | Yellow (6A) |
| Corolla | |
| length | |
| lobes | Reflexed, small |
| Petals: number | Generally 4-many have 5, 6, 7 and 8 on single corolla |
| Pistils | Extend 3/25" to 4/25" above pollen sacs (anthers) of the stamen |
| Number per Node | 2-4' |
| Insertion angle on upright stems | |
| Internodes | ¼" to about 1" |
| Stress Resistance: | |
| Utility Aspects: | Very well suited for container culture |
| **LYNWOOD GOLD** | |
| Plant | |
| Habit | Tall, slender-Upright straight & erect stems |
| Size, height | 6'-7½' |
| Size, width | |
| Vigor | |
| Hardiness | |
| Productivity | Fertile |
| Stems | |
| Color (young) | Green |
| Color (mature) | Brown |
| Rigidity | A bit stiff; pith nodes lamellate; hollow between nodes on one year shoots |
| Leaves | |
| Type | |
| Color | |
| (young) | Deep Green |
| (mature) | Deep Green |
| (fall) | |
| Shape | ovate lanceolate |
| tip | |

TABLE 1-continued

| Ser. No. 271,665 | |
|---|---|
| base | |
| margins | |
| Size | |
| length | 3–4½" |
| width | 1–1½" |
| Venation | |
| Flower | |
| Date of Flowering | Late |
| Size: width | 1"–1½" (medium) |
| Color | Brillant Yellow (lighter than its parent Spectabilis) |
| Corolla | |
| length | |
| lobes | Reflexed |
| Petals: number | Large, broad, open Elliptic |
| Pistils | Extend well above pollen sacs (anthers) of stamens |
| Number per node | |
| Insertion angle on upright stems | |
| Internodes | Flowers almost evenly spaced on stems |
| Stress Resistance | |
| Utility Aspects | |

TABLE 2

| Ser. No. 271,665 FAIRY LAND | |
|---|---|
| Plant | |
| Habit | Small overall & fine textured: Closely spaced flowers & leaves Dense (young) foliage |
| Size, height | 3'–4' |
| Size, width | 5'–6' |
| Vigor | Good vigor for size |
| Hardiness | Zone 6b (or lower) |
| Productivity | Few seed pods |
| Stems | |
| Color (young) | Light green |
| Color (mature) | Brownish green |
| Rigidity | Very flexible lamellate between nodes |
| Leaves | |
| Type | Simple |
| Color | |
| (young) | Medium green (fairly light) |
| (mature) | Medium green (fairly light) |
| (fall) | Mostly faded yellow |
| Shape | Lanceolate |
| tip | Accuminate |
| base | Attenuate |
| margins | On flowering wood; entire On vegetative wood: serrate top ⅓ |
| Size | |
| length | On flowering wood: 1½"–2¼" On vegatative shoots: about 3" |
| width | On flowering wood: 0.2"–0.4" On vegatative shoots 0.5–0.6" |
| Venation | Pinnate |
| Flower | |
| Date of Flowering | Intermediate |
| Size: width | ¾"–1¼" |
| Color | Yellow (6A) |
| Corolla | |
| length | |
| lobes | Reflexed, small |
| Petals: number | Generally 4-many have 5, 6, 7 and 8 on single corolla |
| Pistils | Extend 3/25" to 4/25" above pollen sacs (anthers) of the stamen |
| Number per node | 2–4 |
| Insertion angle on upright stems | |
| Internodes: | ¼" to about 1" |

TABLE 2-continued

| | |
|---|---|
| Stress Resistance | |
| Utility Aspects | Very well suited for container culture |

| Ser. No. 271,666 PYGMY RED | |
|---|---|
| Plant | |
| Habit | Low, loose graceful arching to ground |
| Size, height | 3½'–4½' |
| Size, width | 5'–6' |
| Vigor | Good vigor |
| Hardiness | Hardy Zone 6b (or lower) |
| Productivity | Readily roots where branches touch ground few seed pods |
| Stems | |
| Color (young) | High anthocyanin |
| Color (mature) | Purple Red (59A) |
| Rigidity | Flexible lamellate between nodes |
| Leaves | |
| Type | Simple |
| Color | |
| (young) | Dark Green |
| (mature) | Dark Green |
| (fall) | Anthocyanin (maroon) expressed in full sun |
| Shape | Lanceolate (few lobed leaves on vegetative shoots) |
| tip | Accuminate |
| base | Attenuate |
| margins | Serrate |
| Size | |
| length | 2"–2½" on flowering wood; to 2¾" on vegatative wood |
| width | 0.3"–0.4" on flowering wood; to 1" on vegetative wood |
| Venation | Pinnate |
| Flower | |
| Date of Flowering | Intermediate |
| Size: width | 1¼"–1½" |
| Color | Yellow (7A) |
| Corolla | |
| length | |
| lobes | Narrow |
| Petals: number | 4 - sometimes 5 |
| Pistils | Extend 2/25"–3/25" above pollen sacs of stamens |
| Number per node | 2 |
| Insertion angle on upright stems | |
| Internodes | 1"–1½" (1½" even on fast growing shoots) |
| Stress Resistance | disease and insect |
| Utility Aspects | |

TABLE 3

| Ser. No. 271,665 FAIRY LAND | |
|---|---|
| Plant | |
| Habit: | Small overall & fine textured: Closely spaced flowers & leaves Dense (young) foliage |
| Size, height | 3'–4' |
| Size, width | 5'–6' |
| Vigor | Good vigor for size |
| Hardiness | Zone 6b (or lower) |
| Productivity | Few seeds pods |
| Stems | |
| Color (young) | Light green |
| Color (mature) | Brownish green |
| Rigidity | Very flexible lamellate between nodes |
| Leaves | |
| Type | Simple |
| Color | |
| (young) | Medium green (fairly light) |
| (mature) | Medium green (fairly light) |

TABLE 3-continued

| | |
|---|---|
| (fall) | Mostly faded yellow |
| Shape | Lanceolate |
| tip | Accuminate |
| base | Attenuate |
| margins | On flowering wood: entire<br>On vegetative wood: serrate top ⅓ |
| Size | |
| length | On flowering wood: 1½"–2½"<br>on vegatative shoots: about 3" |
| width | On flowering wood: 0.2"–0.4"<br>On vegetative shoots 0.5–0.6" |
| Venation | Pinnate |
| Flower | |
| Date of Flowering | Intermediate |
| Size: width | ¾"–1¼" |
| Color: | Yellow (6A) |
| Corolla | |
| length | |
| lobes | Reflexed, small |
| Petals: number | Generally 4-many have 5, 6, 7 and 8 on single corolla |
| Pistils: | Extend 3/25" to 4/25" above pollen sacs (anthers) of the stamen |
| Number per node: | 2–4 |
| Insertion angle on upright stems: | |
| Internodes: | ¼" to about 1" |
| Stress Resistance: | |
| Utility Aspects: | Very well suited for container culture |

| | Ser. No. 273,489<br>TINKLE BELLS |
|---|---|
| Plant | |
| Habit: | Semi-dwarf: Upright |
| Size, height | 4'–4½' |
| Size, width | |
| Vigor | Medium vigor |
| Hardiness | Hardy Zone 6b (or lower) |
| Productivity | Does not layer naturally (replicates from stools (no seed pods observed) |
| Stems | |
| Color (young) | Yellow Green |
| Color (mature) | Light brown |
| Rigidity | Sparsely lamellate between nodes - Rigid |
| Leaves | |
| Type | Simple |
| Color | |
| (young) | Medium green |
| (mature) | Medium green |
| (fall) | Faded green to yellow |
| Shape | Elliptical |
| tip | Acute on flower shoots accuminate on vegetative shoots |
| base | |
| margins | serrate on upper ⅓ near tip |
| Size | |
| length | 2"–3" (with petiole) |
| width | ½" |
| Venation | Pinnate |
| Flower | |
| Date of Flowering | Early |
| Size: width | ½"–¾" at 45° angle |
| Color: | Bright Yellow (7B) |
| Corolla | |
| length | ½" open to 45° angle |
| lobes | not reflexed during prime |
| Petals: number | 4; occasionally 5 or 6 |
| Pistils: | short: anthers slightly below stigma portion of pistil |
| Number per node: | 2; often 4 per node |
| Insertion angle on upright stems: | buds & flowers pendulous |
| Internodes: | ½"–1½" |
| Stress Resistance: | Disease and insect |
| Utility Aspects: | Can force flowering suitable for container culture |

TABLE 4

| | Ser. No. 271,665<br>FAIRY LAND |
|---|---|
| Plant | |
| Habit | Small overall & fine textured: Closely spaced flowers & leaves Dense (young) foliage |
| Size, height | 3'–4' |
| Size, width | 5'–6' |
| Vigor | Good vigor for size |
| Hardiness | Zone 6b (or lower) |
| Productivity | Few seed pods |
| Stems | |
| Color (young) | Light green |
| Color (mature) | Brownish green |
| Rigidity | Very flexible lamellate between nodes |
| Leaves | |
| Type | Simple |
| Color | |
| (young) | Medium green (fairly light) |
| (mature) | Medium green (fairly light) |
| (fall) | Mostly faded yellow |
| Shape | Lanceolate |
| tip | Accuminate |
| base | Attenuate |
| margins | On flowering wood: entire<br>On vegetative wood: serrate top ⅓ |
| Size | |
| length | On flowering wood: 1½"–2½"<br>On vegatative shoots: about 3" |
| width | On flowering wood: 0.2"–0.4"<br>On vegatative shoots 0.5–0.6" |
| Venation | Pinnate |
| Flower | |
| Date of Flowering | Intermediate |
| Size: width | ¾"–1¼" |
| Color | Yellow (6A) |
| Corolla | |
| length | |
| lobes | Reflexed, small |
| Petals: number | Generally 4-many have 5, 6, 7 and 8 on single corolla |
| Pistils | Extend 3/25" to 4/25" above pollen sacs (anthers) of the stamen |
| Number per node | 2–4 |
| Insertion angle on upright stems | |
| Internodes | ¼" to about 1" |
| Stress Resitance | |
| Utility Aspects | Very well suited for container culture |

| | Ser. No. 271,919<br>MINIKIN |
|---|---|
| Plant | |
| Habit | Small stature, fine textured; small leaves and small stems; densely foliated |
| Size, height | 2'–2½' |
| Size, width | 3'–4' |
| Vigor | Good vigor but slow growth |
| Hardiness | Zone 6b (or lower) |
| Productivity | Layers naturally<br>Abundant seed pods |
| Stems | |
| Color (young) | Light green |
| Color (mature) | Brownish green |
| Rigidity | Ascending strongly lamellate between nodes |
| Leaves | |
| Type | Simple |
| Color | |
| (young) | Bright green to dark green |
| (mature) | Bright green to dark green |
| (fall) | Fading green until leaf drop |
| Shape | Linear |
| tip | Accuminate |
| base | Attenuate |
| margins | Lightly serrate |

TABLE 4-continued

| | |
|---|---|
| Size | |
| length | On vegetative shoots-1½" attached to ½" long slender petiole; smaller on flowering shoots |
| width | On vegetative shoots - ¼"; |
| Venation | Pinnate |
| Flower | |
| Date of Flowering | Intermediate |
| Size: width | ½"-¾" (cup shaped) fully reflexed |
| Color | Yellow (9A) |
| Corolla | |
| length | |
| lobes | strongly reflexed, very small |
| Petals: number | 4:- short and recurved |
| Pistils | Short; 1/25" below pollen sacs of stamens |
| Number per node | 2-4 |
| Insertion angle on upright stems | |
| Internodes | Short (Flowering shoots ¼-¾" Vegetative shoots up to 2") |
| Stress Resistance | Doesn't require same degree of winter protection as most container grown plants of genre |
| Utility Aspects | Blooming can be forced. Especially suited for container culture. |

TABLE 5

| | Ser. No. 271,665 FAIRY LAND |
|---|---|
| Plant | |
| Habit: | Small overall & fine textured: Closely spaced flowers & leaves Dense (young) foliage |
| Size, height | 3'-4' |
| Size, width | 5'-6' |
| Vigor | Good vigor for size |
| Hardiness | Zone 6b (or lower) |
| Productivity | Few seed pods |
| Stems | |
| Color (young) | Light green |
| Color (mature) | Brownish green |
| Rigidity | Very flexible lamellate between nodes |
| Leaves | |
| Type | Simple |
| Color | |
| (young) | Medium green (fairly light) |
| (mature) | Medium green (fairly light) |
| (fall) | Mostly faded yellow |
| Shape | Lanceolate |
| tip | Accuminate |
| base | Attenuate |
| margins | On flowering wood; entire On vegetative wood: serrate top ⅓ |
| Size | |
| length | On flowering wood: 1½"-2½" On vegatative shoots: about 3" |
| width | On flowering wood: 0.2"-0.4" On vegatative shoots 0.5-0.6" |
| Venation | Pinnate |
| Flower | |
| Date of Flowering | Intermediate |
| Size: width | ¾"-1¼" |
| Color: | Yellow (6A) |

TABLE 5-continued

| | |
|---|---|
| Corolla | |
| length | |
| lobes | Reflexed, small |
| Petals: number | Generally 4-many have 5, 6, 7 and 8 on single corolla |
| Pistils: | Extend 3/25" to 4/25" above pollen sacs (anthers) of the stamen |
| Number per node: | 2-4 |
| Insertion angle on upright stems: | |
| Internodes: | ¼" to about 1" |
| Stress Resistance: | |
| Utility Aspects: | Very well suited for container culture |

| | Ser. No. 272,063 LEMON SCREEN |
|---|---|
| Plant | |
| Habit: | Tall, open and graceful; Upright, fan shape; vigorous; open foliage |
| Size, height | Up to 10' |
| Size, width | Hardy Zone 6b (or lower) |
| Vigor | Vigorous |
| Hardiness | |
| Productivity | Abundant Flowers/highly sterile/ pruned wood branches quickly |
| Stems | |
| Color (young) | |
| Color (mature) | Yellow |
| Rigidity | Slightly lamellate between nodes |
| Leaves | |
| Type | Simple |
| Color | |
| (young) | Yellow green 151 B or Chartreuse (appear after flowering) |
| (mature) | Normal green (Yellow-Green 144) whitish blotches |
| (fall) | Greyed Purple 187 B |
| Shape | |
| tip | Accuminate |
| base | Attenuate |
| margins | Serrate |
| Size | |
| length | Not distinguishing |
| width | Not distinguishing |
| Venation | Pinnate |
| Flower | |
| Date of Flowering | Early |
| Size: width | 1½"-1¾" |
| Color: | Yellow (6C) |
| Corolla | |
| length | |
| lobes | Somewhat reflexed |
| Petals: number | 4, sometimes fasciated |
| Pistils: | aborted stamens &/or pistils |
| Number per node: | 4 to 8 |
| Insertion angle on upright stems: | |
| Internodes: | 1" to 2" long on flowering wood |
| Stress Resistance: | Summer foliage disease & insect resistant |
| Utility Aspects: | Summer pruning leads to shoot with chartreuse leaves (young) |

What is claimed is:

1. A new and distinct cultivar of Forsythia named 'Fairy-Land', substantially as shown and described herein.

* * * * *